US007387877B2

(12) United States Patent
Kraft

(10) Patent No.: US 7,387,877 B2
(45) Date of Patent: Jun. 17, 2008

(54) BIO-SENSOR AND BIO-SENSOR REPORTING SYSTEM

(75) Inventor: Clifford Kraft, Naperville, IL (US)

(73) Assignee: Oro Grande Technology, Naperville, IL (US)

( * ) Notice: Subject to any disclaimer, the term of this patent is extended or adjusted under 35 U.S.C. 154(b) by 273 days.

(21) Appl. No.: 11/098,169

(22) Filed: Apr. 4, 2005

(65) Prior Publication Data

US 2005/0221366 A1 Oct. 6, 2005

Related U.S. Application Data

(60) Provisional application No. 60/559,801, filed on Apr. 6, 2004.

(51) Int. Cl.
*C12Q 1/68* (2006.01)
*C07H 21/02* (2006.01)
*C07H 21/04* (2006.01)

(52) U.S. Cl. ........................ 435/6; 536/23.1; 536/24.3

(58) Field of Classification Search .................... 435/6; 536/23.1, 24.3
See application file for complete search history.

(56) References Cited

U.S. PATENT DOCUMENTS 5,225,167 A * 7/1993 Wetzel ........................ 96/224
5,553,006 A 9/1996 Benda ........................ 364/550
5,750,015 A * 5/1998 Soane et al. ................ 204/454
5,798,945 A 8/1998 Benda ........................ 364/550
5,856,174 A * 1/1999 Lipshutz et al. ......... 435/286.5
5,937,100 A * 8/1999 Kitajima ..................... 382/251
5,968,231 A * 10/1999 Parmentier et al. ............ 95/28
6,043,080 A * 3/2000 Lipshutz et al. ......... 435/287.2
6,046,056 A * 4/2000 Parce et al. ................... 506/39
6,048,498 A * 4/2000 Kennedy ..................... 422/99
6,054,277 A * 4/2000 Furcht et al. .................. 435/6
6,180,536 B1 * 1/2001 Chong et al. ............... 438/745
6,186,660 B1 * 2/2001 Kopf-Sill et al. ........... 366/340
6,194,563 B1 * 2/2001 Cruickshank .............. 536/25.3
6,245,132 B1 * 6/2001 Feldman et al. ............... 96/28
6,816,301 B1 * 11/2004 Schiller ...................... 359/290
6,818,177 B1 * 11/2004 Turcotte ...................... 422/24
6,852,851 B1 * 2/2005 Tooke et al. ............... 536/25.4
6,905,827 B2 * 6/2005 Wohlgemuth et al. ......... 435/6
6,992,181 B2 * 1/2006 Tooke et al. ............... 536/25.4
7,026,121 B1 * 4/2006 Wohlgemuth et al. ......... 435/6
7,109,859 B2 * 9/2006 Peeters .................. 340/539.11
7,217,542 B2 * 5/2007 Tyvoll et al. ............. 435/91.1
2003/0153021 A1 * 8/2003 Lu et al. .................... 435/7.32
2004/0067530 A1 * 4/2004 Gruner ....................... 435/7.1
2004/0211728 A1 * 10/2004 Liu et al. .................... 210/645
2005/0142570 A1 * 6/2005 Parthasarathy et al. ........ 435/6
2005/0142571 A1 * 6/2005 Parthasarathy et al. ........ 435/6
2005/0142663 A1 * 6/2005 Parthasarathy et al. ..... 436/174

OTHER PUBLICATIONS

McBride et al., Autonomous detection of aerosolized *Bacillus anthracis* and *Yersina pestis*. Analytical Chemistry 75: 5293-5299 (2003).*

Baeumner et al., A universal nucleic acid sequence biosensor with nanomolar detection limits. Analytical Chemistry 76: 888-894 (2004).*

Fergenson et al., Reagentless detection and classification of individual bioaerosol particles in seconds. Analytical Chemistry 76: 373-378 (2004).*

Bit World Apr. 6, 2004 Report 2230.html "Infineon Delivers New Biochip System".

* cited by examiner

*Primary Examiner*—Ethan Whisenant
(74) *Attorney, Agent, or Firm*—Clifford Kraft

(57) ABSTRACT

A biosensor unit that can be wall mounted in a location to perform testing of ambient air for bio-contaminants. This unit could contain an air filter for collecting contaminants and a micro-laboratory on a chip or otherwise situated within the unit to perform DNA or RNA binding tests for specific biological targets. Information from such units distributed within an environment could be communicated to one or more central locations via the internet or other communication means to be logged or recorded or to produce reports or alarms.

7 Claims, 4 Drawing Sheets

BIO-SENSOR AND BIO-SENSOR REPORTING SYSTEM

This application is related to and claims priority from U.S. provisional patent application No. 60/559,801 filed Apr. 6, 2004. Application No. 60/559,801 is hereby incorporated by reference.

BACKGROUND

1. Field of the Invention

The present invention relates generally to the field of interior air quality and more particularly to a biosensor reporting system that can track airborne bio-contaminants.

2. Description of the Prior Art

Remote reporting of environmental data in buildings can be accomplished by placing sensors in various locations and then reporting the data back through wires or by wireless to a gathering station. Alternatively sensor units can store data and report back via telephone lines over the internet to a central facility that usually produces a report. Systems also exist that pipe air to a central location for testing.

Current building environmental systems generally collect data including temperature, humidity, carbon dioxide and many times toxics such as carbon monoxide. Some units collect data on particulate content, mold and radon.

Recently various companies have reported "labs on a chip" where entire chemical and DNA matching operations can be performed on a single chip. An example of this technology is the recent announce by the company Infineon of a one half centimeter chip that contains micro-channels that can perform DNA trapping of target DNA in liquid phase of over 400 different DNA target types.

What is badly needed is a reporting system that can collect and report data on airborne pathogens as well as mold, fungi and other airborne biological contaminates.

SUMMARY OF THE INVENTION

The present invention relates to a biosensor unit that can detect specific bio-contaminants in ambient air using DNA, RNA or other tests accomplished by a self-contained micro-laboratory. While DNA and RNA testing is the preferred method of testing, any biological target testing is within the scope of the present invention.

The present invention can contain a collection filter collecting bio-contaminants from ambient air along with a preparation area wherein collected biological air contaminants are prepared for target identification such as by DNA cleaving or any other preparation method, a target identification area wherein the biological air contaminants are matched with biological target models such as DNA or RNA probes, and a detector counting matches of the air contaminates with the biological target models. Usually a counter forms a quantitative measure or figure of concentration of a particular target molecule or substance.

The present invention also relates to using such biological micro-sensors in a network such as the internet to remotely monitor a space for biological contaminants and report it to a location where logging, tabulation or reporting of the data can be made. The system of the present invention can also contain distributed or co-located temperature, humidity and/ or gas sensors. Gas sensors can detect carbon monoxide, carbon dioxide, methane and any other toxic or target gas.

Various drawings and illustrations have been presented to better aid in the understanding of the present invention. The scope of the present invention is not limited to what is shown in the figures.

DESCRIPTION OF THE INVENTION

The present invention relates to a biological sensor and an associated data reporting system that tracks data on airborne pathogens and like bio-contaminants in buildings and other spaces such as aircraft, vessels, vehicles and others. The invention relates generally to an airborne bio-sensor; and a data collection and reporting system.

Figure 1:
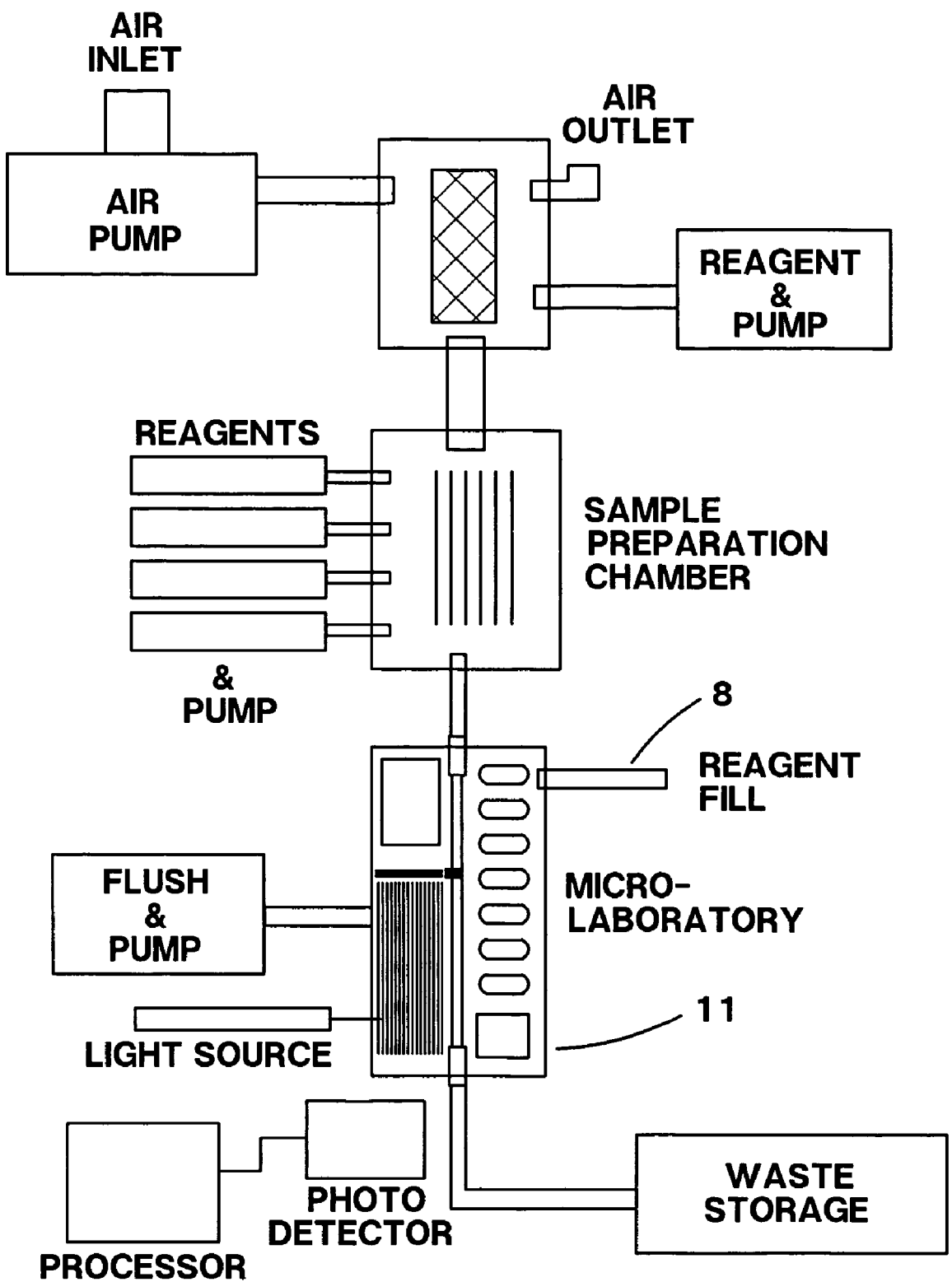
FIG. 1 shows a block diagram of an embodiment of the present invention.

FIG. 1 shows a diagram of an embodiment of an air-borne bio-sensor that can detect DNA of target pathogens. The entire sensor can be mounted or exist on a silicon or other type of chip or can be made in separate units. An optional air pump (seen in the upper left of FIG. 1) can take ambient air and pump or otherwise force it to move into a filter chamber. By pump, I mean any way of moving air through a filter. In the filter chamber, a micro-filter traps airborne contaminants. This filter can be wet or dry; however, to trap very small targets such as viruses, it is desirable that this filter be wet. In either a wet or dry filter, the trapped contaminants are periodically removed using a micro liquid flush. This flush of a pickup reagent can be performed periodically to provide a liquid phase for subsequent reactions. As stated, air can be forced through this trapping filter by means of an external miniature pump or can be allowed to simply pass through by, for example, placing the filter exposure in an HVAC duct. Bio-matter present in the ambient air is generally trapped in the filter.

The second section of the present invention can be a chemical process where raw bio-material is chemically prepared so that half-DNA (or RNA) chains of various genes are exposed. The process of preparing biological samples into split DNA chains is well known. After the half-DNA chains are prepared, they can be labeled with a fluorescent, radioactive or other marking method. This can be seen in the center of FIG. 1 where various reagents are used in a sample preparation chamber to separate and cleave DNA or RNA (or other target material).

The third part of the present invention is normally a laboratory-on-a-chip 11 which contains micro-channels where thousands of target type DNA half-chains can be attached to the walls of the channels using known techniques. These DNA half-chains will bind with only specific target species. The number of target DNA types that can be tested for is constrained only by the number of channels since different channels can contain different target groups. It should be noted that the micro-laboratory does not necessarily need to be located on a single chip, but rather could be in discrete modules or configured in any other manner. While DNA or RNA testing is the preferred method, any other type of biological testing is within the scope of the present invention.

The fluid prepared and tagged in the second section of the device is allowed to enter a particular group of the channels containing the target sensors in the third part of the device shown as a micro-laboratory in FIG. 1. After sufficient exposure time for binding, the chosen channels are flushed and the markers are counted using a photo or radioactive counting technique or any other counting technique depending on the marker type. Various reagents may be used and stored on the chip and can be possibly reloaded by an optional fill tube or device 8.

The key to reuse and hence a device that could last a period of time without being replaced is the use of only a select number of micro-channels on each test run. For example, if a chip contained 10,000 micro-channels, and it was desired to test for 50 different bio-materials or pathogens, the channels could be divided into groups of 50 with the target DNA pattern repeated 2000 times. Many other combinations are possible. Mechanical, magnetostrictive, or magnetic nano-valves could control the exact group of channels that would be used for a given test.

Normally, it would be desirable to flush the used micro-channels after a test to remove excess marker material that would inject noise into subsequent measurements. A flush and pump system draining into a waste storage receptacle could be used as shown in FIG. 1. Also, after each test, the filter could be flushed with material sufficient to remove most of any remaining bio-material before starting the next collection cycle.

Figure 2:
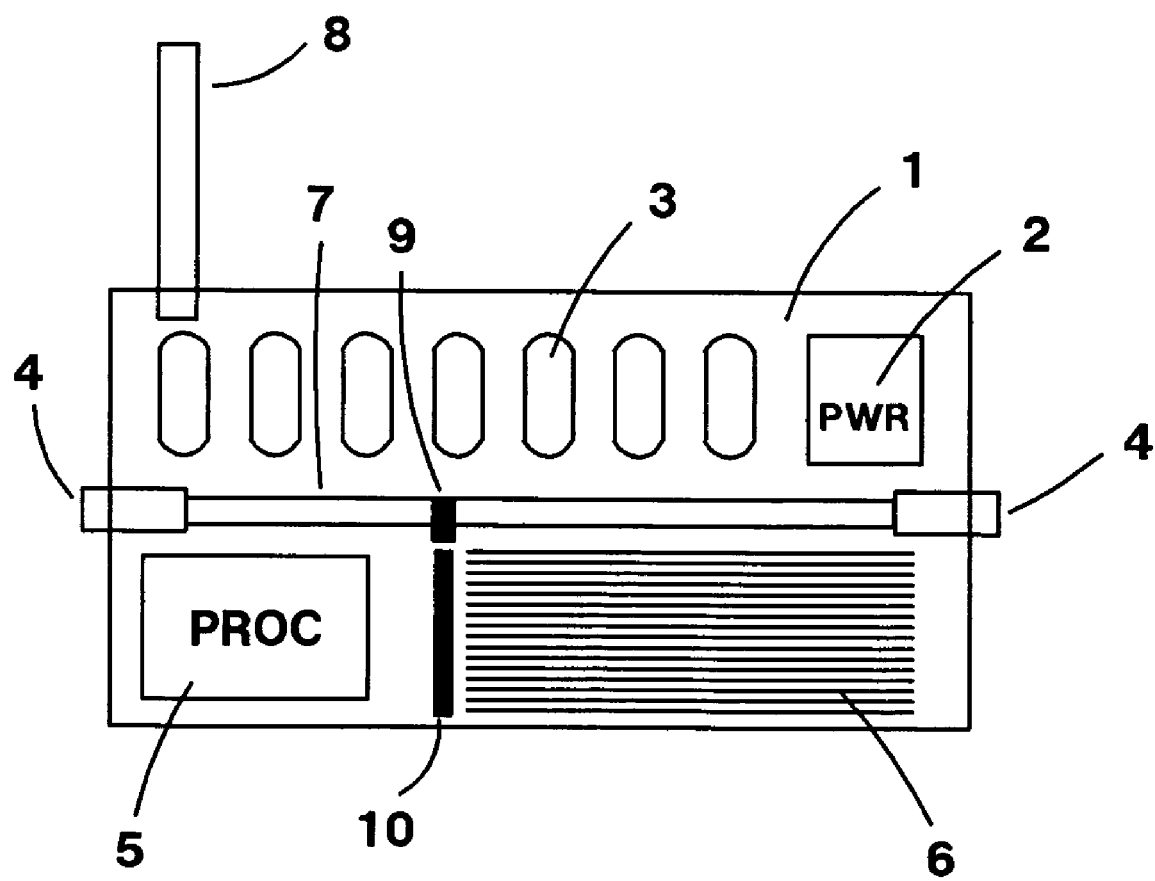
FIG. 2 shows layout of a possible laboratory-on-a-chip.

Turning to FIG. 2, an example layout of a laboratory-on-a-chip 11 is seen. The entire micro-laboratory can be mounted on a substrate 1. A inlet-outlet tube 4 can intersect a valve 9 to route incoming sample fluid into a matrix 10 that directs it into particular micro-channels 6 for testing. Reagents can be stored on the chip in small bins 3 that can also be routed into selected channels 6. These bins 3 can be optionally refilled with reagent by means of a filler 8. An optional power supply 2 and optional processor 5 can control the operation.

Figure 3:
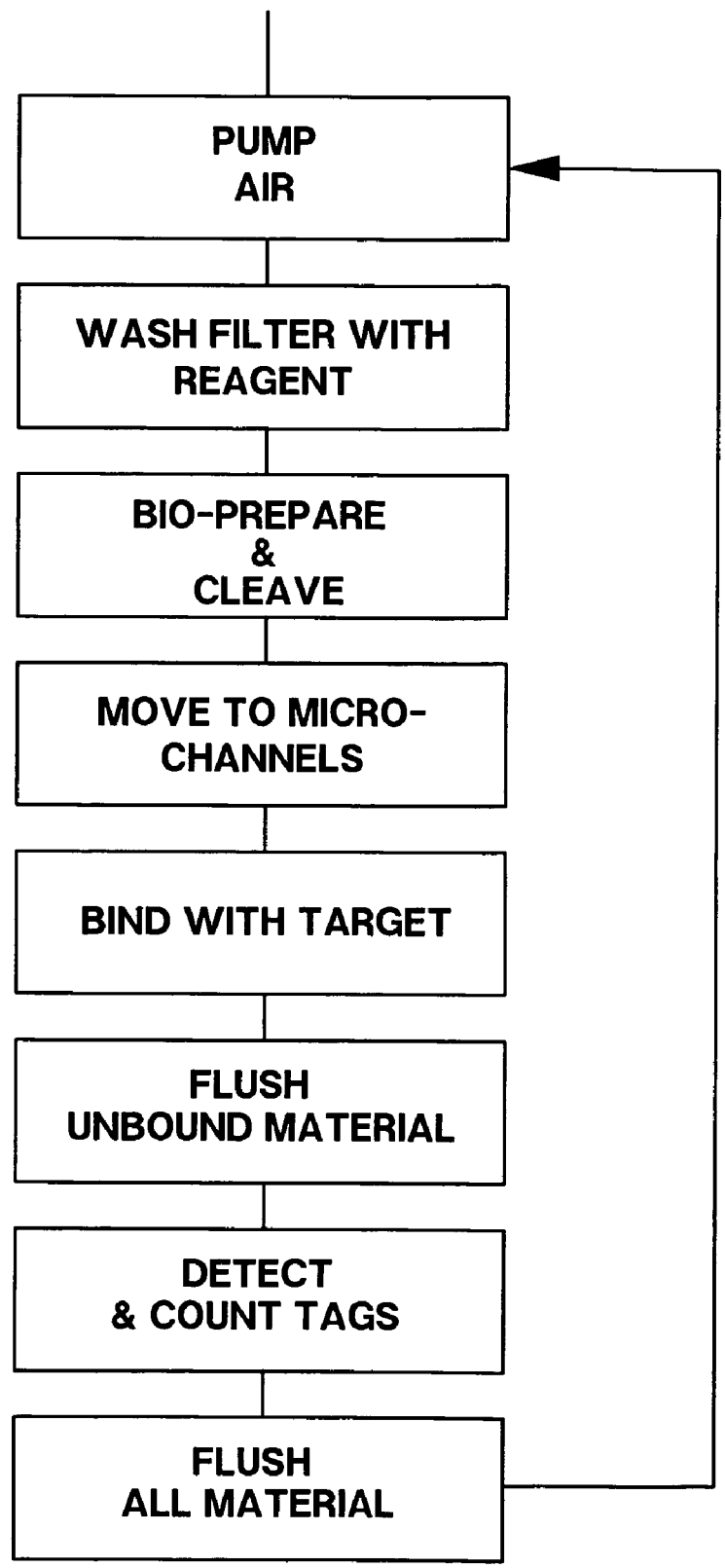
FIG. 3 is a flow chart of a typical air testing process.

An example test sequence in this embodiment is shown in flowchart form in FIG. 3 and could first collect ambient air for a given test period (which would depend on the efficacy of the filter. When enough time had passed to collect enough bio-material to exceed the a noise floor, the filter could be fluidized or washed to collect the material suspended. Possible sampling times could be four to eight hours between washes; however, any times are within the scope of the present invention. The liquid could then be processed and forced into micro-channels for binding. The micro-channels could then be flushed of unbound material. Photo or other counting could then take place and be tallied for each type of target. Finally, the used channels could optionally be totally flushed of all material using an appropriate reagent. Such flushing of used channels would prevent photo-contamination by left over tags on subsequent tests in other channels. The cycle could then be repeated using a different group of channels each cycle.

Figure 4:
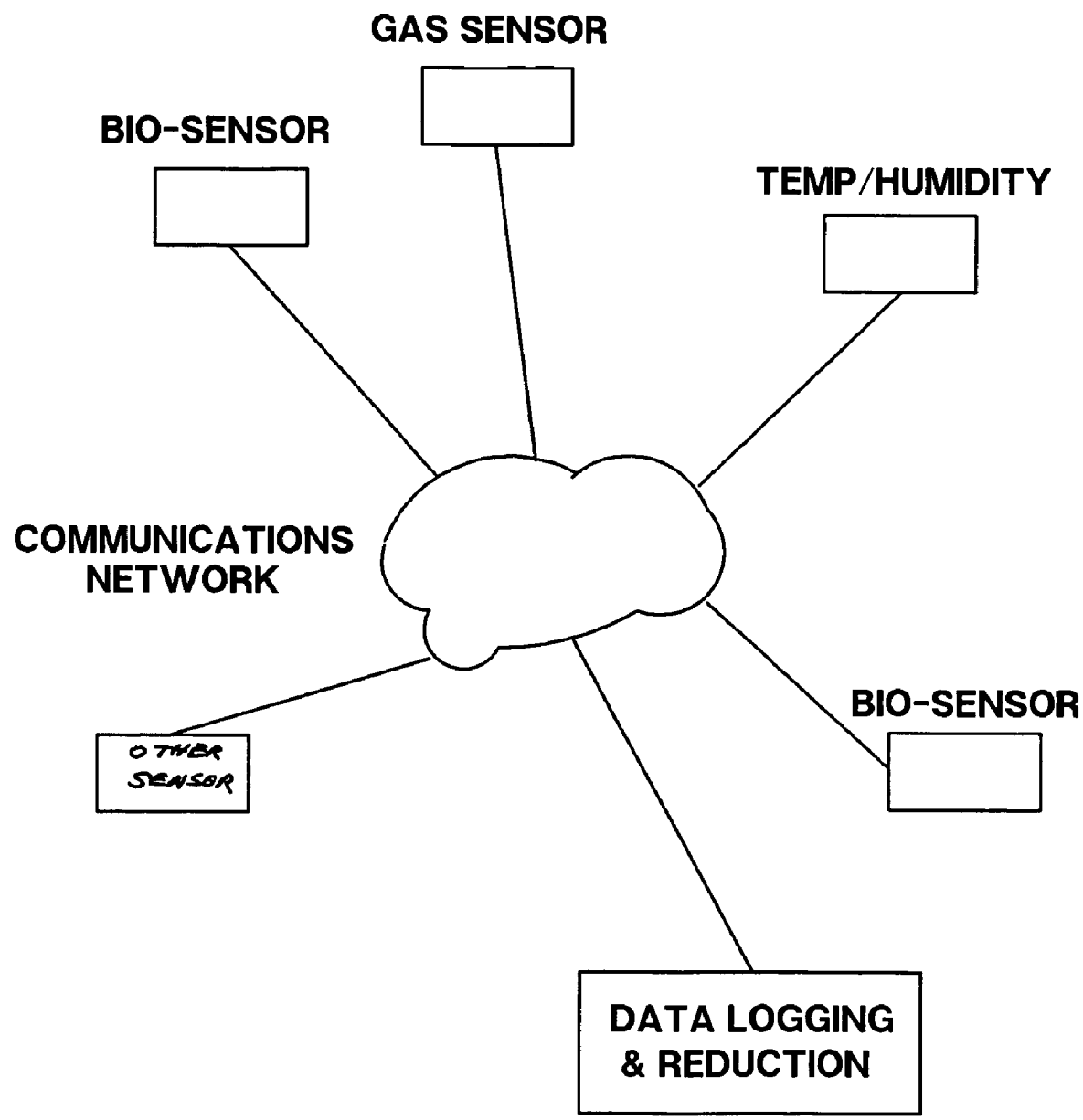
FIG. 4 shows the layout of a building air monitoring system.

An embodiment of a data collection and data reporting system is shown in FIG. 4. Microcontrollers in various distributed biosensor modules can locally control the sequence of testing and store raw counts from the photo circuits. These controllers can then optionally communicate by any means back to a central logging station or can actually log and reduce data itself for direct readout. Typically communication can be by wire, wireless, internet through a telephone line or a wireless link or wireless network, fiber optic or any other communications method. Any type of communication through any type of communication network is within the scope of the present invention.

A biosensor data collection point such as that described could be wall-mounted or could simply be a unit that is placed in position. The unit could accept input data and could be optionally equipped with a visual display. Location data could be entered directly into the unit, or the unit could simply be numbered. GPS could also determine location. Any method of determining where the unit was located when the data was taken is within the scope of the present invention.

One of these units could be moved to different locations, or many such units could be used to simultaneously report data could be used. Communications could take place over the internet or by any other means to one or more central locations where the data could be reduced and trends taken or alarms issued. For example, in a hospital setting, an alarm might be issued if the incidence of a certain pathogen increased beyond a normal level (especially dangerous air-borne pathogens). If more than one test unit were used in a system, the data could be polled or can be reported asynchronously. Also, a unit could report back when it had run out of micro-channels and thus required a chip replacement.

The chip sensor or sensors in a particular reporting unit would normally be replaced at various intervals, either when they ran out of channels, or when it was desired to run tests against different targets. Specialized chips pre-loaded with targets could be available. For example, there could be specialized hospital units that checked an array of common hospital pathogens; there could be mold and fungi units that checked for various species of these bio-contaminants; there could be commercial building indoor air quality units that checked for both some common mold and common pathogens such as flew strains or strains of the common cold.

Reporting units could be combined with other indoor air quality monitoring units to also include temperature, humidity, carbon dioxide, toxics such as CO along with bio-contaminants as shown in FIG. 4.

The present invention has been presented with various descriptions and illustrations. One skilled in the art will recognize that many changes and variations are possible. Such changes and variations are within the scope of the present invention.

I claim:

1. A method of testing ambient air for bio-contaminants comprising the steps of:
   causing ambient air to pass through a collection filter;
   collecting bio-samples from said collection filter, and moving them to a preparation area on a micro-chip;
   preparing said bio-samples for identification in said preparation area;
   moving said bio-samples into at least one channel of a multi-channel micro-laboratory;
   matching said prepared bio-samples against at least one target DNA or RNA sequence in said channel;
   flushing said channel;
   detecting bound bio-samples in said channel.

2. The method of claim 1 wherein the step of preparing comprises cleaving DNA or RNA sequences from said bio-samples.

3. The method of claim 2 wherein the step of preparing further comprises attaching marker molecules to said DNA or RNA sequences.

4. The method of claim 1 wherein the step of detecting comprises measuring light emitted from said bound bio-samples.

5. The method of claim 4 wherein said measuring is performed with a photo-multiplier.

6. The method of claim 1 wherein the step of detecting comprises measure ionizing radiation.

7. The method of claim 1 wherein the step of collecting bio-samples from said collection filter and moving them to a preparation area on a micro-chip comprises causing a liquid to flow through said collection filter.

* * * * *